US00PP19792P2

(12) United States Plant Patent
Danziger

(10) Patent No.: US PP19,792 P2
(45) Date of Patent: Mar. 3, 2009

(54) ***SALVIA* PLANT NAMED 'DANSALCIN1'**

(50) Latin Name: *Salvia coccinea*
Varietal Denomination: DANSALCIN1

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,642

(22) Filed: Jan. 11, 2008

(51) Int. Cl.
*A01H 5/00* (2006.01)

(52) U.S. Cl. ..... Plt./475

(58) Field of Classification Search ..... Plt./263, Plt./475

See application file for complete search history.

*Primary Examiner*—Annette H Para
*Assistant Examiner*—S. B. McCormick Ewoldt

(57) ABSTRACT

A new and distinct *Salvia* cultivar named 'DANSALCIN1' is disclosed, characterized by compact growth, fine, yellow-green foliage, red petals and sepals colored with dark purple. The new variety is a *Salvia,* normally produced as an outdoor garden or container plant.

2 Drawing Sheets

Latin name of the genus and species: *Salvia coccinea.*
Variety denomination: 'DANSALCIN1'.

BACKGROUND OF THE INVENTION

The new cultivar is a product of a planned breeding program conducted by the inventor, Gabriel Danziger. The objective of the breeding program was to produce compact plants of *Salvia coccinea.* Plants of the unpatented variety *Salvia coccinea* 'Coral Nymph' were self-crossed. The new variety was discovered on the Sep. 14, 2005, in Moshav Mishmar Hashiva, Israel by the inventor, Gabriel Danziger, in a group of seedlings resulting from that crossing.

Asexual reproduction of the new cultivar 'DANSALCIN1' by vegetative cuttings was performed at a commercial greenhouse in Moshav Mishmar Hashiva, Israel and has shown that the unique features of this cultivar are stable and reproduced true to type on successive generations.

SUMMARY OF THE INVENTION

The cultivar 'DANSALCIN1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANSALCIN1' These characteristics in combination distinguish 'DANSALCIN1' as a new and distinct *Salvia* cultivar:

1. Compact growth habit.
2. Yellow-Green foliage.
3. Fine foliage texture.
4. Dark purple coloration in sepals.

Plants of the new cultivar 'DANSALCIN1' are similar to plants of the parent, *Salvia coccinea* 'Coral Nymph' unpatented, in most horticultural characteristics, however, plants of the new cultivar 'DANSALCIN1' producer larger flowers than the parent variety. Additionally, flower color of the new variety is red, compared to salmon, of the parent variety.

The parent variety is the best commercial comparison to the new variety 'DANSALCIN1.'

BRIEF DESCRIPTION OF THE PHOTOGRAPH

Figure 1:
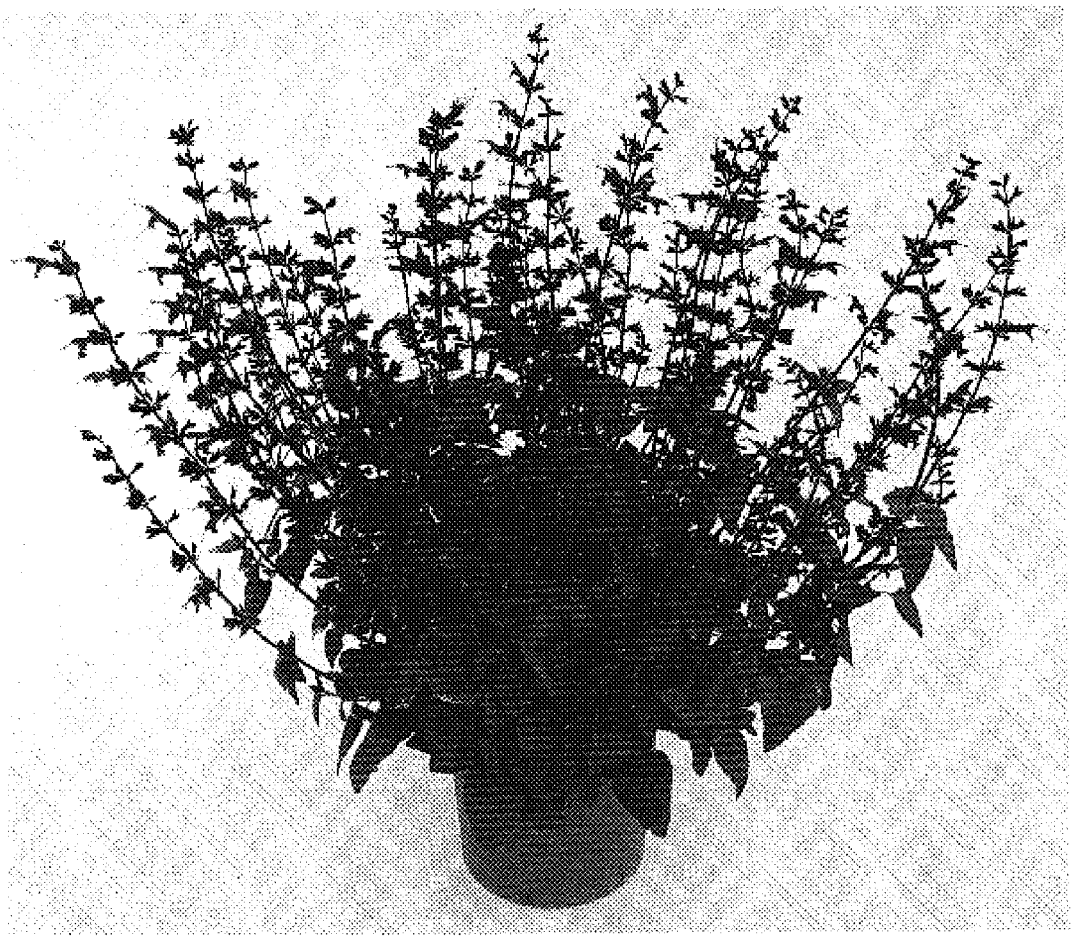

The accompanying photograph in FIG. 1 illustrates in full color a typical plant of 'DANSALCIN1' grown in a greenhouse, in a 1 liter pot. Age of the plant photographed is 9 weeks from a rooted cutting.

Figure 2:
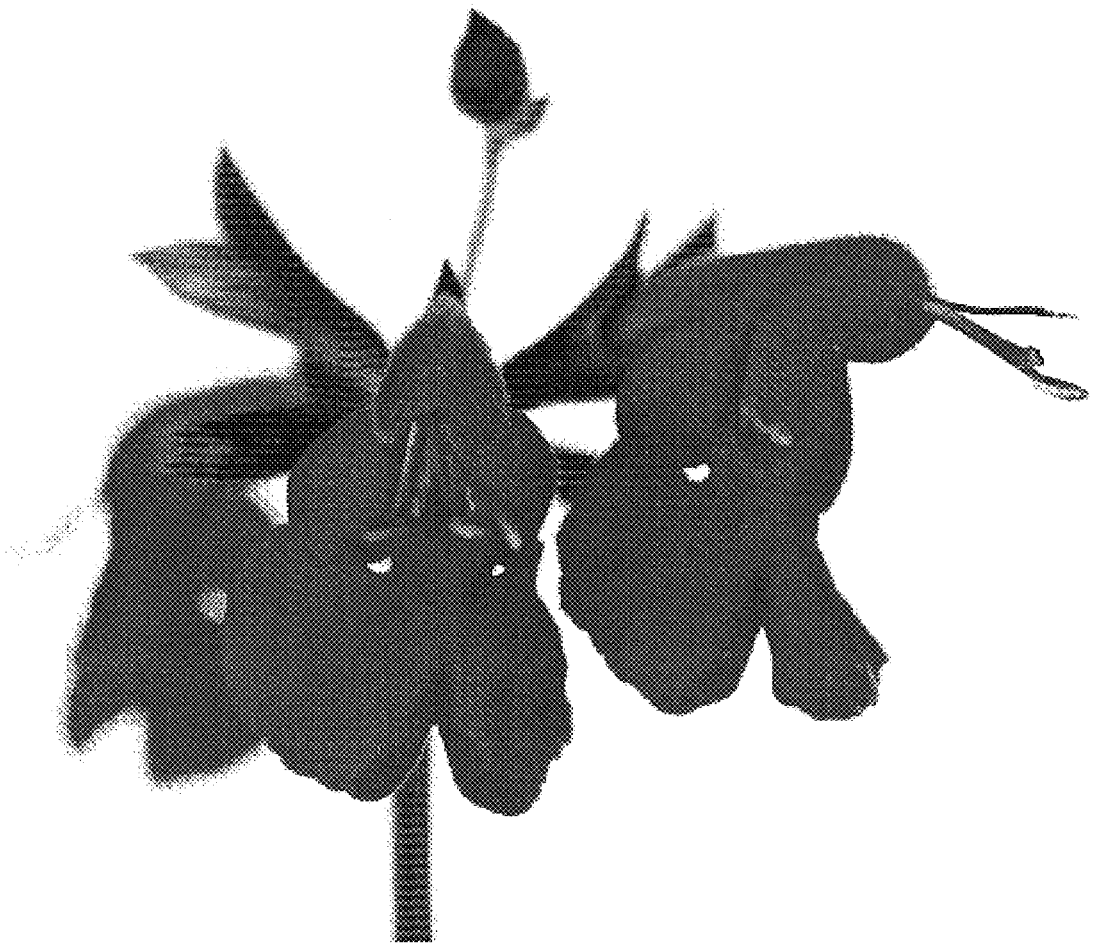

FIG. 2 illustrates in full color a mature typical flower of 'DANSALCIN1' grown in a greenhouse.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANSALCIN1' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Salvia coccinea* cultivar 'DANSALCIN1.'

PROPAGATION

Time to rooting: 5–8 days at approximately 25° C.
Root description: Fine, fibrous.

PLANT

Growth habit: Upright annual.
Pot size of plant described: 12 cm.
Height: Approximately 30 cm.
Plant spread: Approximately 32 cm.
Growth rate: Rapid.

Branching characteristics: Free-branching, Approximately 2 primary branches with lateral branches forming potentially at every node.
Length of primary lateral branches: Approximately 15 cm.
Width of lateral branches: Approximately 65 cm.
Quantity of lateral branches: Approximately 10.
Number of leaves per lateral branch: Approximately 8.
Stem:
*Form.*—Square in cross-section.
*Color.*—Near RHS Green N138A.
*Pubescence.*—Densely pubescent with soft, short hairs.
Internode length: Approximately 15 cm.
Age of plant described: Approximately 6 weeks from a rooted cutting.

FOLIAGE

Leaf:
*Arrangement.*—Opposite.
*Quantity.*—Approximately 8 per main branch.
*Average length.*—Approximately 7 cm.
*Average width.*—Approximately 5 cm.
*Shape of blade.*—Triangular.
*Apex.*—Acute.
*Base.*—Uneven.
*Attachment.*—Stalked.
*Margin.*—Finely dentate.
*Texture of top surface.*—Rough, matte, not glossy.
*Texture of bottom surface.*—Rough, matte, not glossy.
*Leaf internode length.*—Approximately 0.5 cm.
*Color.*—Young foliage upper side: Near RHS Green 137B. Young foliage under side: Near RHS Green 137C. Mature foliage upper side: Near RHS Yellow-Green 147A. Mature foliage under side: Near RHS Green 137B.
*Venation.*—Type: Pinnate. Venation color upper side: Near RHS Yellow-Green 146C. Venation color under side: Near RHS Yellow-Green 146D.
*Petiole.*—Average length. Approximately 4 cm. Color: Near Yellow-Green 146C. Diameter: Approximately 0.2 cm.

FLOWER

Natural flowering season: Free flowering under outdoors growing conditions with substantially continuous blooming from spring through autumn. Year round in greenhouse environment, or under warm conditions and high sunlight. Begins flowering between 5 to 9 weeks of planting a rooted cuttings.
Inflorescence type and habit: Flowers arranged in verticillasters on spikes.
Rate of flower opening: 3 days from bud to fully opened flower.
Flower longevity on plant: Individual flowers last 3 days on the plant. Each spike lasts approximately 5 weeks with flowers.
Quantity of flowers: About 4 buds and 8 fully opened flowers per lateral branch; about 7 blooming spikes per plant.
Inflorescence size:
*Diameter.*—Approximately 4–6 cm.
*Height.*—Approximately 15–25 cm.
Peduncle:
*Length.*—3 cm.
*Diameter.*—0.4 cm.
*Color.*—Near RHS Yellow-Green 144A.
*Orientation.*—Upright, straight.
*Strength.*—Strong.
Corolla:
*Petal arrangement.*—The corolla is sympetalous and typically bilabiate with 2 lobes forming an upper lip and 3 lobes forming a lower lip.
*Size.*—Medium.
*Margin.*—Entire.
*Tip shape.*—Upper lip tip retuse, lower lip tip rounded.
*Length.*—Upper lip Approximately 0.6 cm, lower lip Approximately 1.3 cm.
*Width.*—Upper lip Approximately 0.5 cm, lower lip Approximately 1.5 cm.
*Petal quantity.*—One upper lip and one lower lip with four lobes. Lips are fused at base.
*Petal apex shape.*—Obtuse.
*Texture.*—Smooth, hairless.
*Aspect.*—Horizontal to the stem.
*Petaloids.*—Upper lip has 2 petaloids, lower lip has 4 petaloids.
Color: Petals: When opening:
*Upper surface.*—Near RHS Orange-Red N30A.
*Lower surface.*—Near RHS Red 40C.
Fully opened:
*Upper surface.*—Red group RHS 41A.
*Lower surface.*—Red group RHS 41C.
Bud:
*Shape.*—Ovoid.
*Length.*—Approximately 9 mm.
*Diameter.*—Approximately 3 mm.
*Color.*—Near RHS Red 45A.
Calyx:
*Arrangement.*—Acute angle to stem.
*Height.*—Approximately 0.7 cm.
*Diameter.*—Approximately 0.3 cm.
*Shape.*—Tubular.
Sepals:
*Shape.*—Quantity per flower: 2, fused to form a tube.
*Length.*—Approximately 0.4 cm.
*Width.*—Approximately 0.3 cm.
*Margin.*—Entire.
*Texture.*—Glabrous, surrounded with rough lines.
*Color.*—Immature: Upper surface: Near RHS Purple N79A. Lower surface: Near RHS Purple N77C, with N79A at margin of apex. Mature: Upper surface: Near RHS Brown N77A. Lower surface: Near RHS Yellow-Green 145B, with N79A at margin of apex.
Bracts:
*Quantity.*—2 at the base of each flower.
*Shape.*—Subulate.
*Tip.*—Aristate.
*Texture.*—Glabrous.
*Length.*—Approximately 0.6 cm.
*Width.*—Approximately 0.25 cm.
*Color. Upper surface: Near RHS Yellow-Green* 144B. Lower surface: Near RHS Yellow-Green 144A.
Fragrance: Leaves have strong sage-like odor.

REPRODUCTIVE ORGANS

Stamens:
*Number.*—2.
*Filament length.*—Approximately 2 cm.
Anthers:
*Shape.*—Very narrowly elliptic.
*Length. Approximately* 2 mm.
*Color.*—Near RHS Red 45B, with Grayed-Purple RHS 187C along edge.

*Pollen.*—Color: Near RHS Yellow 8D. Quantity: Not measured.

Pistil:

*Number.*—1.

*Length.*—Approximately 3 cm.

*Style.*—Length: Approximately 2.7 cm. Color: Almost all white Transparent with a touch of RHS Red 46A along edge.

*Stigma.*—Shape: Two-parted, cleft. Color: Near RHS Red 47B Ovary color: Near RHS Yellow-Green 154D.

OTHER CHARACTERISTICS

Seeds and fruits: 4 narrow and oval seeds per flower.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'DANSALCIN1' as herein illustrated and described.

* * * * *